United States Patent
Wilkens

[11] Patent Number: 5,989,283
[45] Date of Patent: Nov. 23, 1999

[54] IRRADIATION DEVICE, ESPECIALLY FOR THE COSMETIC, DIAGNOSTIC AND THERAPEUTIC APPLICATION OF LIGHT

[75] Inventor: Jan Henrik Wilkens, Homburg, Germany

[73] Assignee: Heinrike Wilkens, Homburg, Germany

[21] Appl. No.: 08/937,679

[22] Filed: Sep. 25, 1997

[30] Foreign Application Priority Data

Sep. 26, 1996 [DE] Germany ............................ 196 41 216

[51] Int. Cl.$^6$ .................................................. A61N 21/00
[52] U.S. Cl. .................................. 607/88; 607/93; 606/9; 606/16; 313/110; 250/503.1; 250/493.1; 362/804
[58] Field of Search ............................ 607/88–93; 606/2, 606/9, 10, 13–17; 313/110, 111, 113; 250/493.1, 503.1; 359/227, 232, 234, 236; 362/804

[56] References Cited

U.S. PATENT DOCUMENTS

| | | |
|---|---|---|
| 4,911,166 | 3/1990 | Leighton et al. . |
| 5,220,237 | 6/1993 | Masekit et al. ........................ 313/113 |
| 5,304,173 | 4/1994 | Kittrell et al. ............................ 606/15 |
| 5,320,618 | 6/1994 | Gustafsson . |
| 5,405,368 | 4/1995 | Eckhouse . |
| 5,568,503 | 10/1996 | Omori ...................................... 607/89 |
| 5,755,751 | 5/1998 | Eckhouse ................................ 607/88 |
| 5,769,844 | 6/1998 | Ghaffari ................................... 607/88 |
| 5,814,040 | 9/1998 | Nelson et al. .............................. 606/9 |

FOREIGN PATENT DOCUMENTS

| | | |
|---|---|---|
| 4 95 443 | 7/1992 | European Pat. Off. . |
| 38 59 | 5/1953 | Germany . |
| 26 05 487 | 8/1977 | Germany . |
| 40 08 098 | 9/1991 | Germany . |
| 42 09 957 | 9/1993 | Germany . |

OTHER PUBLICATIONS

Nelson et al., "Dynamic Epidermal Cooling During Pulsed Laser Treatment of Port–Wine Stain," Arch. Dermatol., vol. 131, Jun. 1995.

*Primary Examiner*—Linda C. M. Dvorak
*Assistant Examiner*—Bryan K. Yarnell
*Attorney, Agent, or Firm*—Cohen, Pontani, Lieberman & Pavane

[57] ABSTRACT

An irradiation device, especially for the cosmetic, diagnostic and therapeutic application of light, having an incoherent light source and a reflector that surrounds the light source and has a slit-like opening defining the direction of the radiation. Arranged in the beam path of the light source is a spectral dispersion element. In the output beam path of the spectral dispersion element, a fiber-optic cross-sectional transformer is disposed in such a way that its circular end is located opposite the spectral dispersion element. The fiber-optic cross-sectional transformer and the spectral dispersion element are movable relative to each other.

29 Claims, 4 Drawing Sheets

IRRADIATION DEVICE, ESPECIALLY FOR THE COSMETIC, DIAGNOSTIC AND THERAPEUTIC APPLICATION OF LIGHT

BACKGROUND OF THE INVENTION

1. Field of the Invention

The present invention relates to an irradiation device, especially for the cosmetic, diagnostic and therapeutic application of light, comprising an incoherent light source and a reflector which surrounds the light source and has an opening in the radiation direction of the light source, from which opening the radiation emerges.

2. Description of the Related Art

The therapeutic effect of light has long been known. Various devices that operate in selected spectral ranges are known for various medical syndromes.

DE 40 08 098 discloses a rod-shaped luminaire surrounded axially by a reflector, which has a slit-like opening for the output of light. The opening extends parallel to the longitudinal axis of the luminaire and is formed by the legs of the reflector running toward each other. At their ends, following the nearest approach of the legs to a radius smaller than the curvature radius of the reflector, these legs are bent counter to this curvature. As a result, increased radiation density is attained.

DE-AS 17 64 685 discloses an electric all-purpose discharge lamp with a light-permeable bulb, an electrode pair connectable to a voltage source, an ionizable filling and a covering of luminous substance applied to the bulb inner wall. This lamp produces an output of 6 to 50 $\mu$/W per lumen of visible light in the range above 290 nm wave length, particularly for the middle ultraviolet range, and an output of 150 to 700 $\mu$/W per lumen of visible light for the near ultra violet range. The output in these two ranges is said to be in the ratio of 1:8 to approximately 1:40. It is also stated that the total radiation per lumen is to have roughly the same share as natural daylight of corresponding color temperature. Apart from the fact that the output comparison in 1 m/W is misleading and that non-visible light is being compared to visible light, it can be calculated that a maximum output of 1.5 mW should be emitted for the total range of 290 to 320 nm and a maximum output of 42 mW for the range of 320 to 380. No area reference is given. Further, it is disclosed that lamps of this type can have different maximums into the range of 700 nm, e.g., 570 to 595 or 595 to 625. Overall, the document also discusses prior art related to luminous substance lamps of special wave length, which can have, in contrast to daylight, a sharper maximum at different wave lengths. Suitable luminous substance mixtures are indicated for this purpose, including characteristic metal combinations for different color temperatures. Along with the aforementioned special ratios in the range of UV light, various outputs of natural light compared to selected artificial lamps are shown for lamps with a 40 W rated output and a light output of 2100 to 2300 lm. The goal of that invention is to propose a lamp that, in an 8-hour workday, avoids undesired reddening of the skin (analogous to sunburn) but nonetheless has a desired color reproduction effect. Different biological effects are also mentioned in tabular form, specifically, the effect of light on eye pigmentation, the effect on pineal and gonadal glands of radiation in the wavelength range of 380 to 700 nm, and the bacteria-killing effect of UV light at the 254 nm wavelength. For the UV range, in particular, the formation of vitamins, the de-activation of microorganisms and the cosmetic effect are mentioned. It is also noted that UV radiation can cause changes in the amounts of melanin in the skin. However, this effect is ascribed specifically to the effect of light of the wavelength 290 to 320 nm. It is therefore emphasized that, for this range, less radiation should be provided by the all-purpose lamp with a natural daylight spectrum according to the invention.

DE 31 21 689 C2 proposes a luminous substance lamp that filters by means of the bulb in the UVC and UVB range. The document states that for the UVA range, specifically, a maximum above 350 nm with a spectral width of approximately 320 to 400 nm exists and, in addition, a marked radiation emission in the orange-red range occurs at roughly 650 nm. The intended result is for the luminous substance lamps generally used in solariums (DE OS 26 2B 091) for tanning or for treatment of psoriasis to produce no side effects, such as fatigue or reduced activity. The orange range is meant to have a unilateral influence on nerve tonus and to result in vessel expansion to prevent fatigue. However, the document states that lamps of this type have, in the ranges of 404 and 437 nm (blue), a maximum emission typical of quicksilver and that it is therefore not possible to filter out the blue range as desired according to the description.

DE OS 34 31 692 proposes that a sunlight-like luminous substance lamp with five energy maximums of roughly 320, 380, 450, 550, 650 nm be used. Said energy maximums are to be attained by lamps suitably doped with a mixture of the specified luminous substances. The document notes that cell damage is reparable and eye regeneration is possible in the UVA range, while in the range below 320 nm, long-wave UVB radiation lead to the formation of vitamin D3, calcium resorption, metabolic activation and increased performance of the muscle system and circulatory organs. The document further states that sunburn effects occur only in conjunction with wavelength ranges below 300 nm. For the 300 to 400 nm range, spectral emissions roughly similar to those in the previously cited DE AS 17 64 685 are specified.

In many documents, suitable doping metals are specified for various radiation ranges, e.g., red to dark red (U.S. Pat. No. 3,287,586) or blue (DE OS 19 22 416). Special lamps (DD 201 207 and DD 221 374) have been designed for therapeutic windows around the 325 nm wavelength. DE OS 32 39 417 proposes phosphorous doping for optimized emissions at 340–400 nm for the treatment of skin ailments.

DE 29 10 468 A1 proposes a UV luminous substance radiation source for photobiological and photochemical purposes, particularly for tanning irradiation, wherein the bulb of the radiation source is in contact with a fluid layer, preferably a water layer or water bath. Such a water bath can also be embodied as a water bed with couch, whereby the projection area is a flexible transparent cover of the water bed and the water temperature is set at 30 to 50° C., preferably 35 to 40° C. The document proposes, in detail, an arrangement of the individual radiation sources, which are disposed in gutter-like water containers that surround the luminous substance tubes. The gutter-like elements are equipped with reflectors on the side opposite to the radiation object for the purpose of permitting light reflection from the cooling device toward the projection surface. Also proposed is the use of UV luminous substance lamps in the 300 to 430 nm spectrum with luminous substances that cannot be highly loaded thermally; as applicable, additives are added to the cooling water to influence the spectral transmission grade and/or the reduction in the electrical conductivity. The attainable pigmentation-active radiation output, i.e., the irradiation output, in the aforementioned UV range is put at approximately 140 W/m². Optionally, this irradiation device is also suitable for medical applications (diagnoses and therapy), particularly for the treatment of skin diseases and skin damage. However, the device did not succeed because its main purpose, tanning, can be attained more cheaply with solariums of the traditional type and because the device is too cumbersome and expensive for medical practice. A main reason for this may be that very high demands are placed on the lamps, since the lamp surface temperature of 35 to 40° C., particularly at the relatively high rated output of 115 W, reduces lamp useful life.

It is common to all these devices that the radiation density emitted by them is too low. This leads either to unacceptably long treatment times or to no therapeutic effect at all, since in part the therapeutic effect begins only at a certain radiation density.

A further disadvantage is that for certain spectral ranges (e.g., yellow), there are no suitable doping agents with which suitable radiation densities can be attained. If an attempt is made, by means of suitable filters, to have a broadband light source radiate selectively in these ranges, then the radiation density is further reduced by the filter.

In applications that require high radiation density, it therefore continues to be necessary to use expensive and awkward lasers. The use of different wavelengths after one another, in particular, entails great difficulties with lasers.

From U.S. Pat. No. 5,405,368 a generic device with an incoherent light source is known. The light source is sealed by a glass cylinder and a reflector is arranged around the light source. The cross-section of the reflector is shaped like an ellipse, and the light source is arranged in a focal point of the ellipse. On the side opposite the light source, the reflector has an opening. In front of the opening is arranged a set of optical filters and an iris aperture. A photoflash light is suggested, for example, as the light source. When the device is placed on the body part to be treated, this body part is located at the second focal point of the ellipse. Alternatively, it is suggested that the reflector be designed parabolically and round in cross-section. The iris aperture controls the length and width of the irradiated area, and the maximum length is limited by the length of the light source. Given a proposed lamp length of 8 cm, however, only 5 cm in the center of the lamp is used, whereby approximately uniform radiation occurs. By closing the iris aperture, the length of the irradiated surface can be shortened to a length of 1 mm, as can the width. Given a width of b=5 mm, the width can be shortened by as much as 1 mm by closing the iris aperture. This corresponds to a maximum opening width "d" of one fifth of the diameter. As a result, energy densities in the range of 30 to 100 $J/cm^2$ are attainable. When an optical band pass in the range of 500 to 650 nm is used, the energy density is reduced by 80%, so that energy densities of 6 to 20 $J/cm^2$ are still achieved on the skin.

It is disadvantageous in the known device that the useful life of the optical filter is very short, due to the energy densities, and that the relevant manufacturers do not guarantee functional ability. At the same time, the maximum energy densities attainable are not great enough for the applications "desiccation of veins" and "destroying tatoo pigments."

SUMMARY OF THE INVENTION

An object of the present invention, therefore, is to provide an irradiation device, especially for the cosmetic, diagnostic and therapeutic application of light, which, using an incoherent light source, permits adequate radiation densities to be attained while providing a long useful life of the individual elements.

The present invention is thus directed to a light irradiation device comprising an incoherent light source and a reflector which surrounds the light source and has a slit-like opening in the radiation direction. The arrangement of a spectral dispersion element in the beam path of the light source, in whose output beam path a fiber-optical cross-sectional transformer is disposed in such a way that its circular end is located on the side opposite to the spectral dispersion element so that the fiber-optic cross-sectional transformer and the spectral dispersion element are movable relative to each other, permits a selected spectral range of the light source to be coupled into the fiber-optical cross-sectional transformer with almost no loss.

The light source can be controlled in a pulsed or a continuous fashion. The light source is embodied so as to be laterally movable relative to the reflector and/or is arranged eccentric to the reflector. The reflector is embodied as a metal body with a mirrored inner surface.

In a further embodiment, arranged in the radiation direction of the light source from the slit is a cylindrical elliptical reflector, at whose focal point facing the vertex the light source is arranged. At the second focal point of the cylindrical elliptical reflector, the spectral dispersion element is arranged, whereby the spectral dispersion element can also be embodied in rotatable or pivotable fashion. The fiber-optic cross-sectional transformer arranged in the output beam path of the spectral dispersion element can also be embodied so as to be movable in the vertical and/or horizontal direction and/or in a rotatable and/or pivoting fashion. In a further embodiment, a cylindrical double parabola reflector is used instead of the cylindrical elliptical reflector; in this embodiment the spectral dispersion element is arranged in the direction counter to the radiation direction of the light source.

The reflector surrounding the light source can also consist of an elliptical reflector with an additional concave mirror. The light source is arranged at the focal point facing the vertex of the cylindrical elliptical reflector, while the concave mirror with the slit is arranged at the other focal point of the cylindrical elliptical reflector. The ellipse is sealed by a circular segment having the first focal point as the center point. In this way, all beams are unified in the slit as a matter of principle. The variable adjustment of the width of reflector slit makes it possible to adjust the radiation density or the total emitted radiation depending on the area of application. The spectral dispersion element can be embodied in any design, e.g., as a grating or prism. Further, the device can have associated with it a cooling agent aggregate. The cooling agent aggregate can spray the irradiated skin part with a cooling agent at fixed, programmable time intervals or can be connected actively thereto via a temperature or infrared sensor arranged on the skin part, so that the skin part is sprayed with cooling agent when a settable limit temperature is exceeded. The boiling point of the cooling agent can be between −80° and −10° C. Freon, for example, can be used as the cooling agent. Possible light sources include high-pressure or low-pressure gas discharge lamps known, for example, from other applications, or incandescent lamps, e.g., halogen lamps. In addition, the lamps can be coated with a layer of luminous substance.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF THE PRESENTLY PREFERRED EMBODIMENTS

Figure 1:
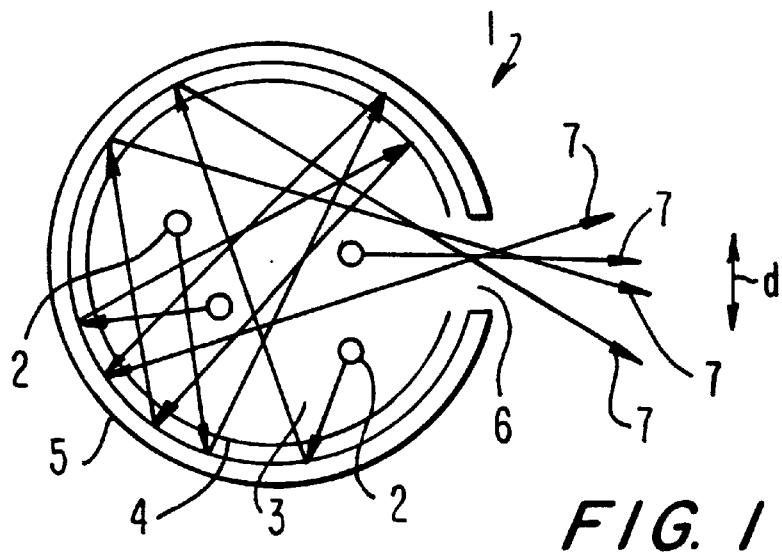
FIG. 1 shows a cross-section through the device with a light source and surrounding reflector.

The irradiation device 1 comprises a light source 3 filled with gas molecules 2 and enclosed by a glass cylinder 4. Arranged around the glass cylinder 4, resting on or at a distance from the glass cylinder 4, is a cylindrical reflector 5, which has a slit 6 of the width d, which extends in the longitudinal direction of the reflector 5. The light source 3 is, for example, a known xenon discharge lamp 300 mm in length and 10 mm in diameter. The reflector surrounding the light source 3 can be slit over the full length or only partially. The width d of the slit 6 is smaller than $U/(4 \times \pi)$ of the reflector 5, where U is the circumference of the closed reflector 5. The luminous substance tubes produce diffuse radiation 7 in a wide spectral range. A small portion of the radiation 7 emerges directly through the slit 6, while most of the diffuse radiation 7 strikes the reflector 5. There the radiation 7 is reflected, with a small portion of approximately 1% being absorbed upon each incident of reflection. The radiation 7 is reflected on the reflector 5 until the radiation 7 falls on the slit 6 and is able to emerge. Thus, the slit 6 defines the radiation direction of the light source 3.

Figure 2:
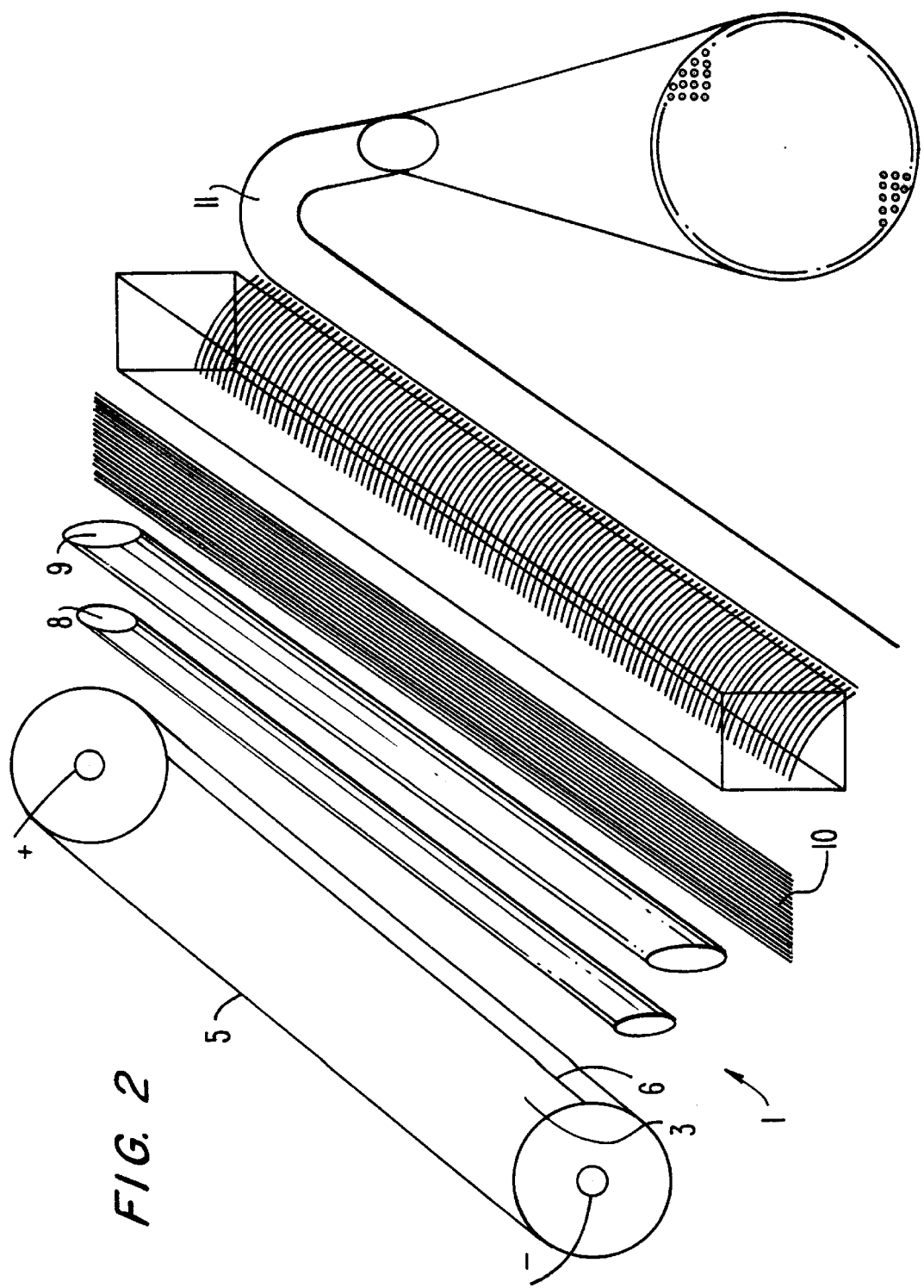
FIG. 2 shows a schematic depiction, in perspective, of a device with a surrounding reflector and further components.

FIG. 2 shows a schematic view of the irradiation device 1 in perspective. The irradiation device 1 comprises the light source 3 with the reflector 5, which surrounds the light source 3 and has the slit 6. Arranged in the radiation direction of the light source 3 is a condenser 8 with small focal distance, at whose focal plane a further condenser 9 with large focal distance is arranged. A spectral dispersion element 10 is arranged on the focal plane of the condenser 9. The spectral dispersion element 10 is embodied, for example, as a grating or prism. Arranged in the output beam path of the spectral dispersion element 10 is a fiber-optic cross-sectional transformer 11. The fiber-optic cross-sectional transformer 11 has dimensions of, for example, 300 mm×0.3 mm on the side facing the spectral dispersion element 10 and a circular cross-sectional of approximately 1 cm diameter on the side opposite the spectral dispersion element 10. The radiation emerging from the slit 6 of the reflector 5 strikes the condenser 8 and is reproduced by the latter on the condenser 9. The condenser 8 acts, together with the condenser 9, as the collimator. The condenser 9 reproduces the radiation onto the spectral dispersion element 10, where the radiation is spectrally dispersed. The spectral dispersion element 10 and/or the fiber-optic cross-sectional transformer 11 are embodied to be movable and/or rotatable, so that they can be adjusted relative to each other in such a way that the spectrally dispersed radiation is reproduced on the input of the fiber-optic cross-sectional transformer 11. The radiation emerging from the circular cross-sectional of the fiber-optic cross-sectional transformer 11 can then be used directly for irradiating a patient. By moving the spectral dispersion element 10 or the fiber-optic cross-sectional transformer 11, fine spectral scanning can be implemented, in that only selected frequency ranges are coupled into the fiber-optic cross-sectional transformer 11.

Figure 3:
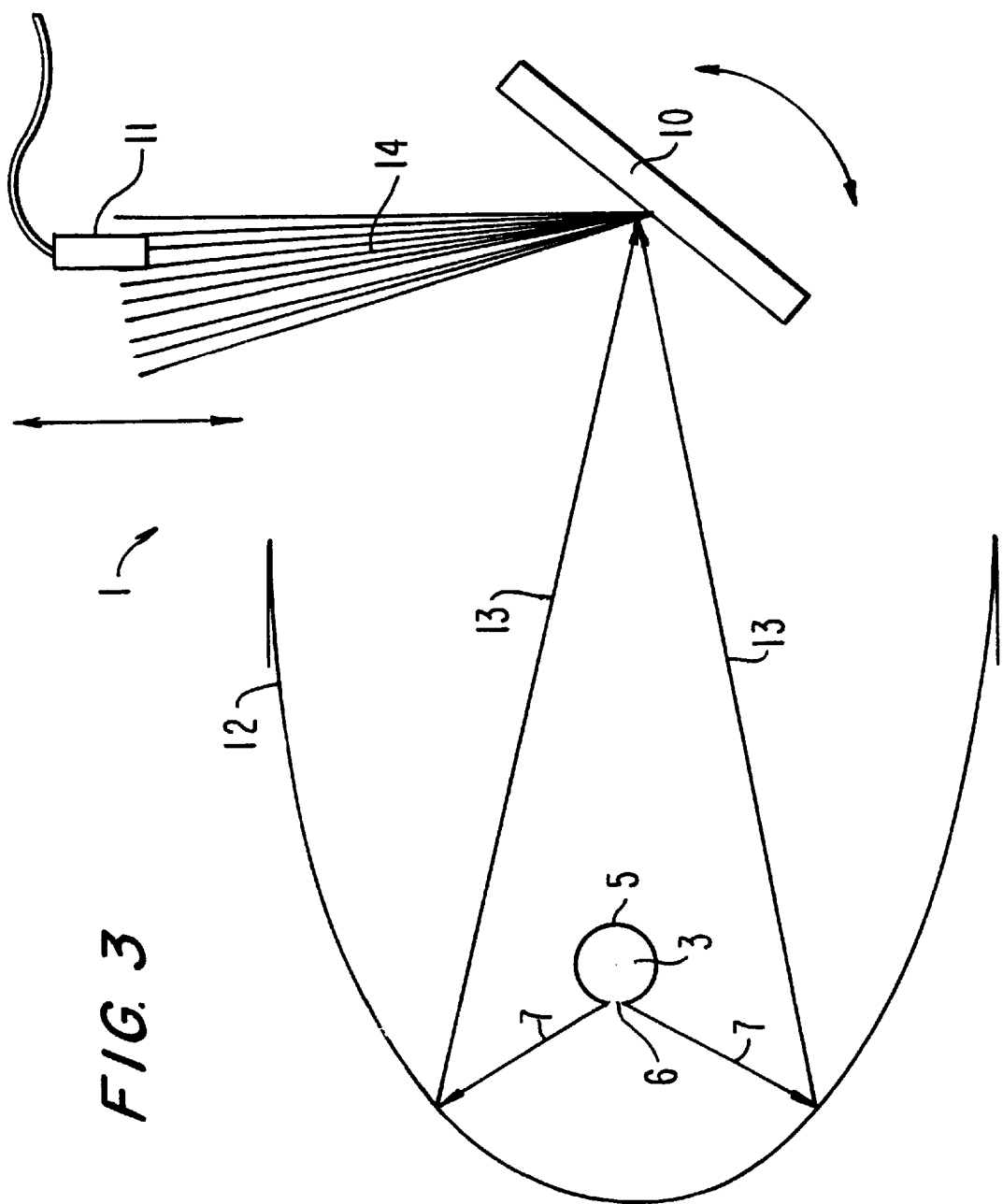
FIG. 3 shows a cross-sectional through a further device with a surrounding reflector and an additional reflector.

FIG. 3 shows a device 1 with a double reflector structure. Arranged in the radiation direction of the light source 3 from the slit 6 of the reflector 5 is a cylindrical elliptical reflector 12. The light source 3 is arranged at the focal point facing the vertex of the cylindrical elliptical reflector 12. At the other focal point of the cylindrical elliptical reflector 12, the spectral dispersion element 10 is arranged, which is embodied in rotatable fashion. Arranged in the output radiation path of the spectral dispersion element 10 is the fiber-optic transformer 11, which is embodied movably. Along with having the vertical mobility shown, the fiber-optical cross-sectional transformer 11 can also be designed, as needed, to be movable horizontally. The beam 7 emerging from the light source 3 through the slit 6 of the reflector 5 strikes the inner wall of the cylindrical elliptical reflector 12. The cylindrical elliptical reflector 12 reflects the beam 7 onto the second focal point of the cylindrical elliptical reflector 12. At the second focal point, the reflected radiation 13 strikes the spectral dispersion element 10 and is split by this element 10 spectrally. The spectral dispersion element 10 in this embodiment is preferably designed as a grating. Arranged in the beam path of the grating radiation 14 is the fiber-optic cross-sectional transformer 11, into which a certain spectral portion of the grating radiation 14 is coupled, based on the position of the spectral dispersion element 10 relative to the fiber-optical cross-sectional transformer 11. By moving the fiber-optic cross-sectional transformer 11 in the horizontal direction, it is possible to select a certain spectral range; this can also be done by rotating the spectral dispersion element 10. The bandwidth of the spectral range that is coupled in the fiber-optical cross-sectional transformer 11 can be varied by the vertical movement of the fiber-optical cross-section transformer 11, so that the entire spectrum can be coupled in as needed.

Figure 4:
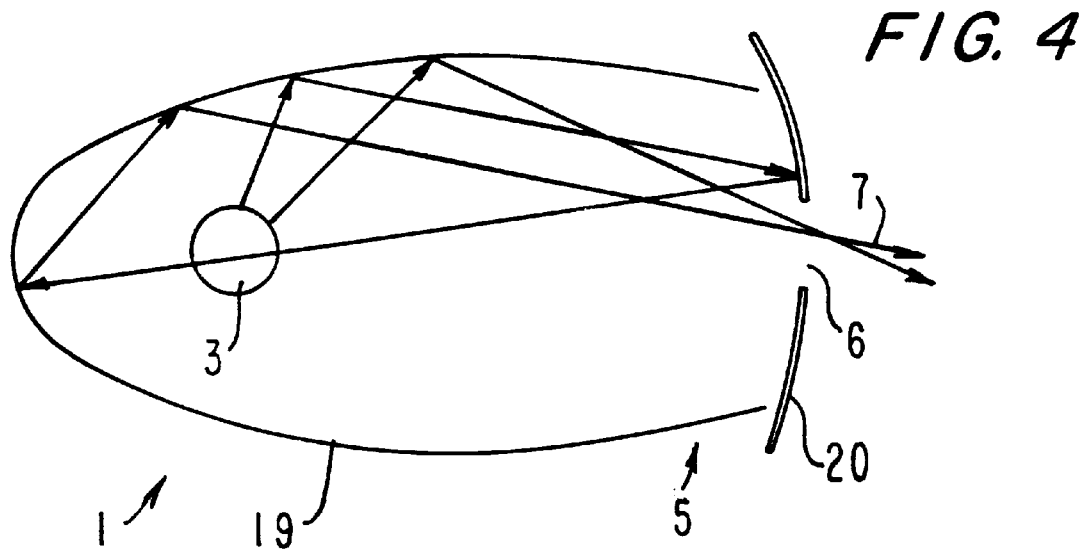
FIG. 4 shows a cross-sectional through a further device with a light source and a reflector surrounding the light source, which device consists of a cylindrical elliptical reflector with a concave mirror.

FIG. 4 shows a further possible embodiment of the irradiation device 1. The reflector 5 surrounding the light source 3 consists of a cylindrical elliptical reflector 19 and a concave mirror 20. The light source 3 is arranged in a focal point facing the vertex of the cylindrical elliptical reflector 19. At the other focal point of the cylindrical elliptical reflector 19 the concave mirror 20 is arranged, which has a slit 6. Due to the properties of the ellipse, namely the reproduction of one focal point onto the other focal point, a larger share of the radiation 7 emitted by the light source 3 emerges without prior reflection directly from the slit 6, so that the attainable radiation output density increases further.

When a 300 mm photoflash lamp with a flash energy of 8000 J is used, a flash output density of 90 J/cm² in attained. By designing the slit 6 with a width "d" smaller than $U/(4 \times \pi)$, the output density can be increased to over 1000 J/cm², so that, assuming coupling losses of 50%, an effective energy density of over 500 J/cm² is attained. If the spectrum extending from approximately 200 to 1200 nm is dispersed into five equal-sized wavelength ranges, an effective energy density of approximately 100 J/cm² per wavelength range is still achieved. This even exceeds current-day solid lasers, whose thinner beams must first be artificially widened with the help of an X-Y scanner to avoid skin injuries. Along with the applications already mentioned, use in endoscopes is possible. For example, very bright illumination in the blue UV range is possible, where, via a 1 mm fiber, a 1000 mW light output can be applied, which corresponds to the light output of approximately 1000 blue LEDs. As a consequence of this bright illumination, it is also possible to perform steady state fluorescent detection with chip endoscopes without image intensification. Furthermore, solid lasers previously used in photodynamic therapy in the red spectral range around 635 nm can be replaced.

Figure 5:
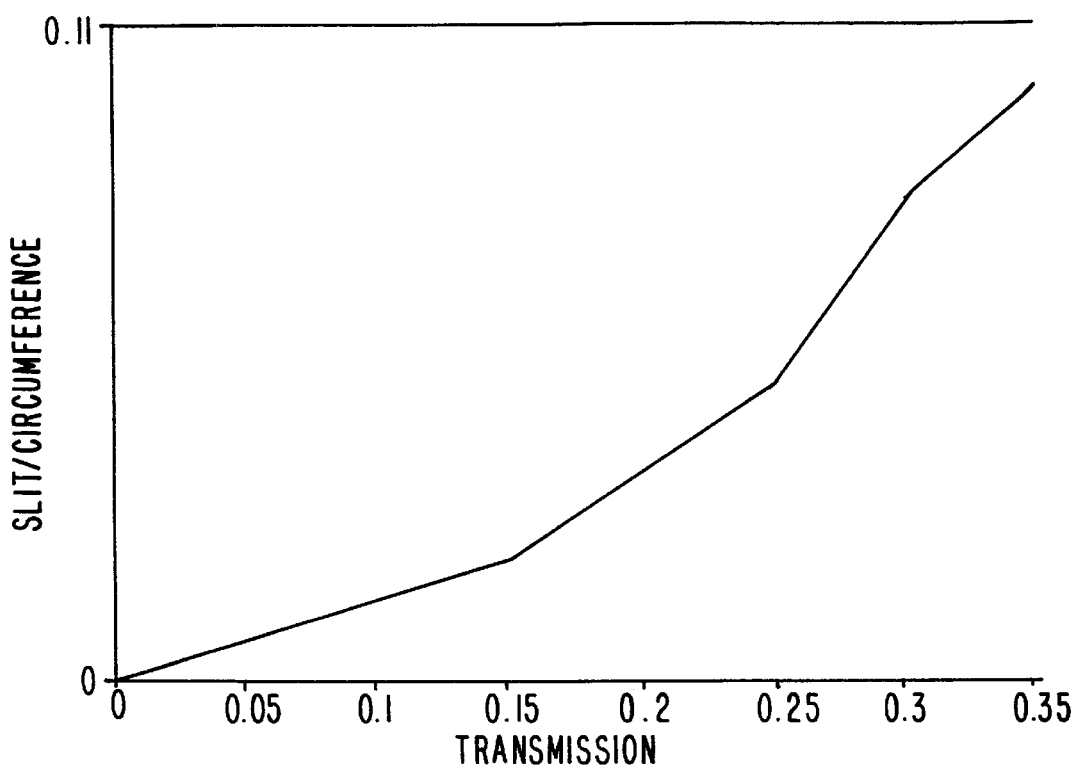
FIG. 5 is a diagram of the total radiated output in % over the slit width/circumference ratio.
Figure 6:
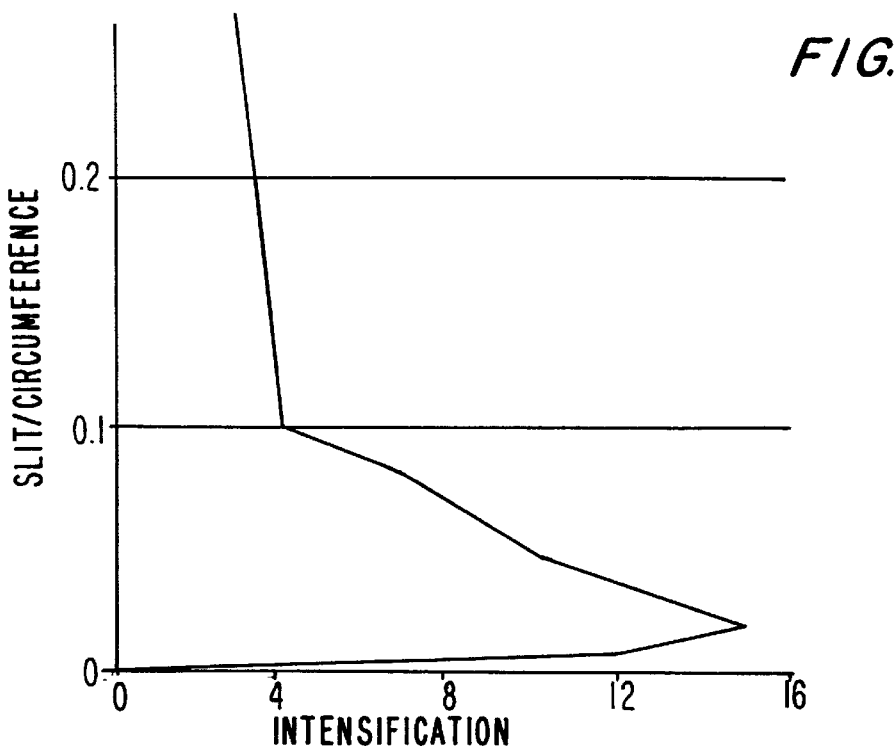
FIG. 6 is a diagram of the intensification of the output density via the slit width/circumference ratio.

The diagram in FIG. 5 indicates that the radiated total output in % declines in monotone fashion when a slit 6 with a reduced width "d" is used. However, as FIG. 6 shows, output density increases monotonously, due to intensification, until an absolute maximum is reached. The subsequent drop in intensification in the case of very small slit widths is attributable to the disproportionate increase in reflections. The curves shown in the drawings were measured with a cylindrical light source surrounded by a cylindrical reflector 5.

The present invention is not limited by the embodiments described above which are presented as examples only but can be modified in various ways within the scope of protection defined by the appended patent claims.

What is claimed is:

1. A light irradiation device, comprising:
   an incoherent light source;
   reflector surrounding the light source and having a slit-like opening defining a radiation direction of the light source and a beam path, said slit-like opening having a width "d" which is less than $U/(4\times\pi)$ wherein U is a circumference of the reflector in a closed condition;
   a spectral dispersion element arranged in the beam path of the light source and having an output beam path;
   a fiber-optic cross-sectional transformer having a circular end and arranged in the output beam path of the spectral dispersion element in such a way that the circular end of the cross-sectional transformer is located opposite the spectral dispersion element, the fiber-optic cross-sectional transformer and the spectral dispersion element being movable relative to each other; and
   a cylindrical elliptical reflector arranged in the radiation direction of the light source from the slit-like opening, the cylindrical elliptical reflector having a first focal point facing a vertex of the cylindrical reflector and a second focal point located opposite the vertex of the cylindrical reflector, the light source being arranged at the first focal point and the spectral dispersion element being arranged at the second focal point.

2. The light irradiation device of claim 1, wherein the reflector consists of a cylindrical elliptical reflector and a concave mirror, the cylindrical elliptical reflector having a first focal point facing a vertex of the reflector and a second focal point located opposite the vertex of the reflector, wherein the concave mirror has the slit-like opening, the light source is arranged at the first focal point, and the concave mirror is arranged at the second focal point.

3. The light irradiation device of claim 1, wherein the slit-like opening width "d" is variably adjustable.

4. The light irradiation device of claim 1, wherein the light source is at least one of being laterally movable relative to the reflector and being arranged eccentric to the reflector.

5. The light irradiation device of claim 1, wherein the reflector includes a metal body with a mirrored inner surface.

6. The light irradiation device of claim 1, wherein the spectral dispersion element is embodied in at least one of a rotatable and pivotable fashion.

7. The light irradiation device of claim 1, wherein a collimator is arranged between the light source and the spectral dispersion element.

8. The light irradiation device of claim 7, wherein the collimator comprises an input side of a first condenser having a focal plane and a small focal distance, and an output side of a second condenser having a focal distance relatively larger than the focal distance of the first condenser, the second condenser being arranged on the focal plane of the first condenser.

9. The light irradiation device of claim 1, wherein the device has associated with it a cooling agent aggregate for spraying irradiated skin with a cooling agent at fixed, programmable time intervals.

10. The light irradiation device of claim 9, wherein the boiling point of the cooling agent is between −80° and −10° C.

11. The light irradiation device of claim 1, wherein the device has associated with it a cooling agent aggregate which is actively connected to a temperature sensor or infrared sensor arranged on an irradiated skin part, such that, when an adjustable temperature limit is exceeded, sprays the skin part with a cooling agent.

12. The light irradiation device of claim 11, wherein the boiling point of the cooling agent is between −80° and −10° C.

13. The light irradiation device of claim 1, wherein the light source is a halogen lamp.

14. The light irradiation device of claim 13, wherein the lamp is coated with a layer of luminous substance.

15. The light irradiation device of claim 1, wherein the fiber-optic cross-sectional transformer is embodied so as to be movable in at least one of a vertical and horizontal direction and in at least one of a rotatable and pivotable fashion.

16. A light irradiation device, comprising:
   an incoherent light source;
   a reflector surrounding the light source and comprising a cylindrical elliptical reflector and a concave mirror, the cylindrical elliptical reflector having a first focal point facing a vertex of the reflector and a second focal point located opposite the vertex of the reflector, wherein the concave mirror has a slit-like opening, the light source is arranged at the first focal point, and the concave mirror is arranged at the second focal point wherein the slit-like opening defines a radiation direction of the light source and a beam path, said slit-like opening having a width "d" which is less than $U/(4\times\pi)$ wherein U is a circumference of the reflector in a closed condition;
   a spectral dispersion element arranged in the beam path of the light source and having an output beam path; and
   a fiber-optic cross-sectional transformer having a circular end and arranged in output beam path of the spectral dispersion element in such a way that the circular end of the cross-sectional transformer is located opposite the spectral dispersion element, the fiber-optic cross-sectional transformer and the spectral dispersion element being movable relative to each other.

17. The light irradiation device of claim 16, wherein the slit-like opening width "d" is variably adjustable.

18. The light irradiation device of claim 16, wherein the light source is at least one of being laterally movable relative to the reflector and being arranged eccentric to the reflector.

19. The light irradiation device of claim 16, wherein the reflector includes a metal body with a mirrored inner surface.

20. The light irradiation device of claim 16, wherein the spectral dispersion element is embodied in at least one of a rotatable and pivotable fashion.

21. The light irradiation device of claim 16, wherein a collimator is arranged between the light source and the spectral dispersion element.

22. The light irradiation device of claim 21, wherein the collimator comprises an input side of a first condenser having a focal plane and a small focal distance, and an output side of a second condenser having a focal distance relatively larger than the focal distance of the first condenser, the second condenser being arranged on the focal plane of the first condenser.

23. The light irradiation device of claim 16, wherein the device has associated with it a cooling agent aggregate for spraying irradiated skin with a cooling agent at fixed, programmable time intervals.

24. The light irradiation device of claim 23, wherein the boiling point of the cooling agent is between −80° and −10° C.

25. The light irradiation device of claim 16, wherein the device has associated with it a cooling agent aggregate which is actively connected to a temperature sensor or infrared sensor arranged on an irradiated skin part, such that, when an adjustable temperature limit is exceeded, sprays the skin part with a cooling agent.

26. The light irradiation device of claim 25, wherein the boiling point of the cooling agent is between −80° and −10° C.

27. The light irradiation device of claim 16, wherein the light source is a halogen lamp.

28. The light irradiation device of claim 16, wherein the lamp is covered with a luminous substance.

29. The light irradiation device of claim 20, wherein the fiber-optic cross-sectional transformer is embodied so as to be movable in at least one of a vertical and horizontal direction and in at least one of a rotatable and pivotable fashion.

* * * * *